(12) United States Patent
Rittmeyer et al.

(10) Patent No.: US 10,144,651 B2
(45) Date of Patent: Dec. 4, 2018

(54) METHOD FOR PRODUCING APROTIC SOLUTIONS THAT CONTAIN ZINC BROMIDE AND LITHIUM BROMIDE

(71) Applicant: Rockwood Lithium GmbH, Frankfurt am Main (DE)

(72) Inventors: Peter Rittmeyer, Sulzbach/Taunus (DE); Johannes Willems, Frankfurt am Main (DE); Dieter Hauk, Friedberg (DE); Uwe Lischka, Frankfurt am Main (DE); Florian Kiefer, Goslar (DE); Dirk Dawidowski, Friedberg (DE)

(73) Assignee: ALBEMARLE GERMANY GMBH (DE)

( * ) Notice: Subject to any disclaimer, the term of this patent is extended or adjusted under 35 U.S.C. 154(b) by 176 days.

(21) Appl. No.: 15/109,489

(22) PCT Filed: Dec. 19, 2014

(86) PCT No.: PCT/EP2014/078757
§ 371 (c)(1),
(2) Date: Jul. 1, 2016

(87) PCT Pub. No.: WO2015/101524
PCT Pub. Date: Jul. 9, 2015

(65) Prior Publication Data
US 2016/0326007 A1 Nov. 10, 2016

(30) Foreign Application Priority Data
Jan. 3, 2014 (DE) .................. 10 2014 200 007

(51) Int. Cl.
| C01G 9/04 | (2006.01) |
| C07F 3/06 | (2006.01) |
| C01B 9/04 | (2006.01) |
| C01D 15/04 | (2006.01) |

(52) U.S. Cl.
CPC .............. *C01G 9/04* (2013.01); *C01B 9/04* (2013.01); *C01D 15/04* (2013.01); *C07F 3/06* (2013.01); *C01P 2006/82* (2013.01)

(58) Field of Classification Search
CPC .... C01G 9/04; C07F 3/06; C01B 9/04; C01D 15/04; C01P 2006/82
See application file for complete search history.

(56) References Cited

U.S. PATENT DOCUMENTS

| 2004/0033191 A1 | 2/2004 | Wietelmann et al. |
| 2005/0207968 A1 | 9/2005 | Jungkamp et al. |
| 2013/0142721 A1 | 6/2013 | Wietelmann et al. |

FOREIGN PATENT DOCUMENTS

| DE | 10 2011 005 499 A1 | 9/2011 |
| EP | 1380539 A2 | 1/2004 |
| WO | 3029329 A1 | 5/2000 |
| WO | 2004007371 A1 | 1/2004 |

OTHER PUBLICATIONS

Dieter et al.; "Zinc Compounds"; Ullmann's Encyclopedia of Industrial Chemistry; Jun. 15, 2000; Wiley-VCH Verlag GmbH & Co. KGaA, Weinheim, Germany; pp. 748-752.
"Zink Bromide"; Gmelins Hanbuch Der Anorganischen Chemie; Jan. 1, 1956; p. 885.
"Lithium Bromide"; Gmelins Hanbuch Der Anorganischen Chemie; Jan. 1, 1960; p. 410.
"Lithium Bromide"; Ullmann's Encyclopedia of Industrial Chemistry, Fifth, Completely Revised Edition; vol. A 15; Jan. 1, 1990; p. 407.
Lemaire et al.; "Stereoselective C-Glycosylation Reactions with Arylzinc Reagents"; Organic Letters 2012; vol. 14, No. 6; pp. 1480-1483.

*Primary Examiner* — Peter F Godenschwager
*Assistant Examiner* — Andrew J. Oyer
(74) *Attorney, Agent, or Firm* — Jeremy J. Kliebert

(57) ABSTRACT

The invention relates to a method for producing aprotic solutions that contain zinc bromide and lithium bromide, the reaction of the reactants to the product being carried out as a one-pot reaction.

19 Claims, No Drawings

METHOD FOR PRODUCING APROTIC SOLUTIONS THAT CONTAIN ZINC BROMIDE AND LITHIUM BROMIDE

CROSS-REFERENCE TO RELATED APPLICATIONS

This application is a National Stage of International Application No. PCT/EP2014/078757, filed on Dec. 19, 2014, which application claims priority from German Patent Application No. 10 2014 200 007.6, filed Jan. 3, 2014. Each patent application identified above is incorporated here by reference in its entirety.

BACKGROUND

Zinc organic compounds play an increasingly important role in organic synthesis in the production of pharmaceuticals, agrochemicals and other fine chemicals. Most of all because of their good compatibility with a variety of functional groups, they are important intermediates in organic chemistry. In addition to direct insertion of Zn metal into organic halides, they can be prepared by transmetallation of Li- or Mg-organic compounds. In special cases, a transmetallation of an organolithium compound using a solution of $ZnBr_2$ and LiBr, for example in dibutyl ether, enables special transformations such as the stereoselective C-glycosylation of arylzinc reagents (S. Lemaire, I.N. Houpis, T. Xiao, J. Li, E. Digard, C. Gozlan, R. Liu, A. Gavryushin, C. Diene, Y. Wang, V. Farina and P. Knochel, *Stereoselective C-Glycosylation Reactions with Arylzinc Reagents*, Org. Lett 2012, 14, 1480-1483).

Zinc bromide and lithium bromide are prepared by the reaction of cheap raw materials such as zinc oxide, zinc carbonate, zinc metal, lithium hydroxide or lithium carbonate with hydrobromic acid in an aqueous medium. The solid salts are obtained by crystallization or evaporation of the reaction solutions. The solids thus produced are then dissolved in dibutyl ether.

For the transmetallation reactions named above, the most-anhydrous solution possible of zinc bromide and lithium bromide in dibutyl ether is required. To accordingly produce the anhydrous solids, long drying times and/or high drying temperatures are required. After drying, the solids must be packaged, and must likewise be dissolved in dibutyl ether in a manner which excludes moisture.

It would therefore be desirable to produce zinc bromide and lithium bromide from cheap raw materials directly in the desired solvent, dibutyl ether. The process should directly produce an anhydrous solution, or it should be possible to easily remove from the system any water of reaction which may form.

DETAILED DESCRIPTION

The problem addressed by the invention is that of providing an economical synthesis of a solution of $ZnBr_2$ and LiBr in aprotic solvents. Because the organometallic compounds used in this application react quickly and completely with water, thereby reducing the yield of the reaction, the solution of $ZnBr_2$/LiBr in dibutyl ether should have the lowest possible water content.

According to the invention, the method for producing aprotic solutions containing zinc bromide and lithium bromide is carried out in such a way that the reactants are converted to the product in a one-pot reaction, wherein the water which is formed is removed azeotropically and the product solution is obtained with a residual water content <2500 ppm.

Alternatively, the method for producing aprotic solutions containing zinc bromide and lithium bromide is carried out in such a way that aqueous solutions of zinc bromide and lithium bromide are mixed in a stoichiometric ratio and an aprotic solvent is added thereto in such a volume that the water which is present is removed azeotropically and a product solution is obtained with a residual water content <2500 ppm.

The first method can be carried out according to the invention by dispersing zinc oxide or zinc carbonate and lithium carbonate or lithium hydroxide, as starting materials, in an aprotic solvent, reacting the same with aqueous hydrobromic acid (HBr) in an aprotic solvent, removing the water which forms azeotropically, and separating the product solution from the unreacted starting materials. Surprisingly, a suspension of the starting materials (ZnO, $Li_2CO_3$) in an organic "non-solvent" reacts with aqueous HBr to produce the desired products. Even at a temperature of no more than 145° C., and atmospheric pressure, it is possible to remove all but residual water amounts of 1200 to 100 ppm from the reaction mixture. By lowering the pressure during the azeotropic distillation, the required temperature can be further lowered. Experience has shown that, for drying an aqueous LiBr solution, at least 180° C. and a good vacuum are required. The inventive method allows the use of cheaper starting materials such as zinc oxide, zinc carbonate, zinc metal, and lithium carbonate or lithium hydroxide. These are suspended in dibutyl ether and converted by the addition of aqueous hydrobromic acid into their bromides. Dibutyl ether and water form an azeotrope which boils at 95° C., such that the water introduced with the hydrobromic acid, and the water of reaction, can then be removed by azeotropic distillation. The desired product solution is prepared in a one-pot process from cheap raw materials without the need to first isolate, package, transport, and dissolve the hygroscopic and corrosive solids in dibutyl ether.

Alternatively, the method can be carried out according to the invention by dispersing a mixture of metallic zinc and metallic lithium as the starting materials in an aprotic solvent and reacting the same with elemental bromine, then separating the product solution from the unreacted starting materials, or by dispersing a mixture of metallic zinc and lithium metal as the starting materials in an aprotic solvent and reacting the same with hydrogen bromine, then separating the product solution from the unreacted starting materials. LiBr is virtually insoluble in dibutyl ether. Surprisingly, this insoluble LiBr does not deposit on the metal surface, which would then prevent a further reaction. It has been found that even Li metal structures with a smaller surface, such as Li granules, react quantitatively.

One possible scientific explanation could be that in the selected reaction medium Li and Zn react with similar reaction rates with $Br_2$ and/or HBr, and can form a 1:X complex of $LiBr:ZnBr_2$ which is soluble in dibutyl ether before the surface of the metal is blocked by insoluble LiBr, wherein X is a number>1.

Surprisingly, gaseous, anhydrous HBr dissolves in the reaction medium dibutyl ether to such an extent that it is available in a sufficient concentration for a reaction with the metals.

Ether can be used advantageously in the method according to dc invention as the aprotic solvent. The use of an aliphatic ether of the general formula $R^1$-O-$R^2$, where $R^1$ and $R^2$ are each an alkyl moiety with 1 to 10 carbon atoms, is particularly preferred. It is most particularly preferred that dibutyl ether is used.

The zinc is advantageously used in powder form with an average particle size of 20 to 600 μm, and the lithium is used as granules having an average particle size of 1 to 3 mm. The metals zinc and lithium can be used both as coarser pieces and as a fine powder.

The method according to the invention is carried out in the temperature range from −20 to 100° C., and particularly preferably in the temperature range from 0 to 40° C.

EXAMPLE(S)

The invention is described in more detail below with reference to three examples, without thereby restricting the invention to these examples.

Example 1

220 g dibutyl ether is filled into a 0.5-L jacketed reactor. 30.7 g (377 mmol) of zinc oxide and 13.7 g (185.4 mmol) of lithium carbonate are suspended in this solvent at room temperature. Via a dropping funnel, 187 g of aqueous hydrobromic acid (48.5%=1121 mmol HBr) is added dropwise over a period of 30 minutes. Zinc bromide and lithium bromide are formed in an exothermic reaction (with evolution of $CO_2$). At the end of the reaction, two clear, colorless liquid phases are found in the reaction vessel. The water in the reaction mixture is removed by azeotropic in this process, the outer shell temperature of the jacketed reactor is gradually increased from 130° C. to 180° C. Initially, water is removed quickly. As the volume of evaporated water increases, the rate decreases significantly. After about 8 hours, the water separation is complete, and the reaction solution has a boiling point of 144-145° C.

Analysis of the reaction solution:
Zn 1.2 mmol/g
Li 1.2 mmol/g
Br 3.6 mmol/g
$H_2O$ 500 ppm Example 2

220 g dibutyl ether, 2.62 g (375.7 mmol) of lithium granules and 25.15 g (384 mmol) of Zn powder are filled into a 0.5-L jacketed reactor. Via a dropping funnel, 89.95 g (563.6 mmol) elemental bromine is added over 80 minutes. The reaction temperature of the exothermic reaction is limited by cooling to about 25° C. The mixture is allowed to react for a further 2 hours at 25° C. The two metals dissolve almost completely. The brown/red product solution is isolated from the excess metal by decanting.

Analysis of the product solution:
$H_2O$ 700 ppm

Example 3

175 g dibutyl ether, 2.1 g (330.5 mmol) of lithium granules and 20.6 g (315 mmol) of Zn powder are filled into a 0.5-L jacketed reactor. 73.5 g (908 mmol) of gaseous HBr is introduced into the reaction solution from a compressed gas cylinder. The start of the reaction can be recognized by the temperature descent and by the onset of gas evolution (hydrogen). The duration of HBr bubbling is about 90 minutes, and the reaction temperature is limited by cooling the double jacket to about 25° C. To complete the reaction, the heat is briefly raised to 45° C. after the reagent has finished being added. Excess metal can be easily removed by filtration through a Schlenk frit. The reaction product obtained is a water-clear, colorless solution.

Zn 1.12 mmol/g
Li 0.98 mmol/g
Br 3.12 mmol/g
$H_2O$ 2200 ppm

Example 4

186 g dibutyl ether is filled into a 0.5-L jacketed reactor with a water separator and heated at 350 mbar to boiling (boiling point about 105° C.). 238 g of an aqueous solution of $ZnBr_2$ and LiBr (12.2% LiBr, 34.2% $ZnBr_2$) is added continuously over a period of about 5 hours. The water is continuously removed from the system by azeotropic distillation. After the addition of solution is ended, the mixture is boiled under reflux until no more water separates.

Zn 1.2 mmol/g
Li 1.1 mmol/g
$H_2O$ 700 μm

The invention claimed is:

1. A method for producing an aprotic solution containing zinc bromide and lithium bromide, the method comprising:
   dispersing starting materials in an aprotic solvent, wherein the starting materials comprise (i) zinc oxide or zinc carbonate, and (ii) lithium carbonate or lithium hydroxide;
   reacting the starting materials dispersed in the aprotic solvent with hydrobromic acid to form a reaction mixture; and
   removing water from the reaction mixture to form a product solution
   with a residual water content <2500 ppm; and
   separating the product solution from unreacted starting materials.

2. The method according to claim 1 wherein the aprotic solvent is an ether.

3. The method according to claim 1, wherein the aprotic solvent is an aliphatic ether having a general formula of $R^1$—O—$R^2$, where $R^1$ and $R^2$ are each an alkyl moiety with 1 to 10 carbon atoms.

4. The method according to claim 1 wherein the aprotic solvent is dibutyl ether.

5. The method according to claims 1 wherein the reaction is carried out in a temperature range from −20° C. to 100° C.

6. The method according to claim 1 wherein the reaction is carried out in a temperature range from 0° C. to 40° C.

7. A method for producing an aprotic solution containing zinc bromide and lithium bromide, the method comprising:
   mixing aqueous solutions of zinc bromide and lithium bromide in a stoichiometric ratio, and
   adding an aprotic solvent thereto in volume sufficient to remove water which is present to form the aprotic solution with a residual water content <2500 ppm.

8. The method according to claim 7 wherein the aprotic solvent is an ether.

9. The method according to claim 7, wherein the aprotic solvent is an aliphatic ether having a general formula of $R^1$—O—$R^2$, where $R^1$ and $R^2$ are each an alkyl moiety with 1 to 10 carbon atoms.

10. The method according to claim 7 wherein the aprotic solvent is dibutyl ether.

11. The method according to claims 7 wherein the reaction is carried out in a temperature range from −20° C. to 100° C.

12. The method according to claim 7 wherein the reaction is carried out in a temperature range from 0° C. to 40° C.

13. A method for producing an aprotic solution containing zinc bromide and lithium bromide, the method comprising
   dispersing starting materials in an aprotic solvent, wherein the starting materials comprise a mixture of metallic zinc and metallic lithium;

reacting the starting materials dispersed in the aprotic solvent with hydrogen bromide or elemental bromine to form a product solution; and separating the product solution from unreacted starting materials.

14. The method according to claim 13 wherein the metallic zinc and metallic lithium are in a form of powder, coarse pieces, or both powder and coarse pieces.

15. The method according to claim 13 wherein the aprotic solvent is an ether.

16. The method according to claim 13, wherein the aprotic solvent is an aliphatic ether having a general formula of $R^1$—O—$R^2$, where $R^1$ and $R^2$ are each an alkyl moiety with 1 to 10 carbon atoms.

17. The method according to claim 13 wherein the aprotic solvent is dibutyl ether.

18. The method according to claim 13 wherein the reaction is carried out in a temperature range from −20° C. to 100° C.

19. The method according to claim 13 wherein the reaction is carried out in a temperature range from 0° C. to 40° C.

* * * * *